(12) United States Patent
Iwashita et al.

(10) Patent No.: US 8,298,481 B2
(45) Date of Patent: Oct. 30, 2012

(54) METHOD FOR STERILIZING A PLASTIC BOTTLE

(75) Inventors: Takeshi Iwashita, Kanagawa (JP); Yonosuke Takahara, Kanagawa (JP); Kenichi Kominami, Kanagawa (JP); Ken Isogawa, Kanagawa (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 0 days.

(21) Appl. No.: 13/317,436

(22) Filed: Oct. 18, 2011

(65) Prior Publication Data
US 2012/0076689 A1   Mar. 29, 2012

Related U.S. Application Data

(62) Division of application No. 12/925,808, filed on Oct. 29, 2010, now Pat. No. 8,124,011, which is a division of application No. 11/989,848, filed as application No. PCT/JP2006/315889 on Aug. 4, 2006, now Pat. No. 7,906,069.

(30) Foreign Application Priority Data
Aug. 4, 2005   (JP) ................. 2005-226537

(51) Int. Cl.
*A61L 9/00*   (2006.01)
*A61L 2/08*   (2006.01)
*B65B 55/04*   (2006.01)
*B08B 9/00*   (2006.01)
*B08B 1/02*   (2006.01)

(52) U.S. Cl. .......... 422/1; 422/32; 422/33; 422/26; 422/27; 422/28; 422/303; 422/304; 53/426; 134/22.12; 134/22.13; 134/22.14; 134/15; 134/25.1; 99/275; 99/323.1

(58) Field of Classification Search .......... 422/1, 32–33, 422/303–304, 26–28; 53/426; 134/22.12, 134/22.13, 22.14, 15, 25.1; 99/275, 323.1
See application file for complete search history.

(56) References Cited

U.S. PATENT DOCUMENTS
3,531,908 A * 10/1970 Tuma et al. ............... 53/426
6,596,231 B1 * 7/2003 Catelli et al. .............. 422/28

FOREIGN PATENT DOCUMENTS
EP   1 086 896 A1 *   3/2001
* cited by examiner

Primary Examiner — Jill Warden
Assistant Examiner — Monzer Chorbaji
(74) Attorney, Agent, or Firm — Hedman & Costigan, P.C.; James V. Costigan

(57) ABSTRACT

A method for sterilizing a plastic bottle in an aseptic filling system according to which at least an inner surface or an outer surface of a bottle is sterilized by injecting a heated sterilizing fluid at 65° C.-90° C. while maintaining internal pressure of the bottle at 1 kPa-20 kPa.

5 Claims, 3 Drawing Sheets

METHOD FOR STERILIZING A PLASTIC BOTTLE

This application is a divisional application of application Ser. No. 12/925,808, filed Oct. 29, 2010 now U.S. Pat. No. 8,124,011, which is a divisional application of application Ser. No. 11/989,848, filed Jan. 31, 2008 now U.S. Pat. No. 7,906,069, which claims the benefit of PCT/JP2006/315889, filed Aug. 4, 2006 which claims the priority of JP-2005-226537, filed Aug. 4, 2005.

TECHNICAL FIELD

This invention relates to a method for sterilizing a plastic bottle such as a PET bottle in an aseptic filling system.

BACKGROUND ART

There has recently been an increasing tendency toward adopting an aseptic filling system as a method for filling contents in a container capable of preventing deterioration of flavor caused by heating contents such as a drink. In a case where the container is a plastic bottle such as a PET bottle in the aseptic filling system, there is generally adopted a method according to which hot water or a heated sterilizer such as peracetic acid, hydrogen peroxide or alkali is injected from a mouth portion of the bottle onto an inner surface of the bottle before filling contents such as a drink thereby to sterilize at least the inner surface of the bottle. In this case, there is the problem that the bottle must have resistance (strength) to heat corresponding to a sterilizing temperature and, if the sterilizing temperature exceeds the heat resisting temperature, thermal shrinkage occurs in the bottle resulting in deformation of the bottle.

Particularly in recent years, there is an increasing social demand for reducing weight of a bottle. As a bottle becomes lighter, there is a tendency to decrease in thickness of a trunk portion of the bottle and, therefore, the problem of occurrence of thermal shrinkage has become prominent.

As a method for sterilizing the inner surface of the bottle without causing thermal shrinkage in a non-heat resistant plastic bottle such as a PET bottle, there has generally been adopted a method for sterilizing an inner surface of a bottle by injecting hot water or a heated sterilizer at a temperature below 70° C., avoiding a temperature range from 70° C. to 95° C. which is a normal sterilizing temperature and a temperature which causes thermal shrinkage. Japanese Patent Application Laid-open Publication No. 2003-181404, for example, discloses a method for sterilizing a bottle by injecting a heated sterilizer from a first nozzle onto an inner surface of an inverted bottle and also storing a predetermined amount of the sterilizer in a mouth portion of the bottle, and stirring and raising this stored sterilizer by a sterilizer injected from a second nozzle whereby a part of the sterilizer staying in a mouth portion of the bottle is scattered over the inner surface of the bottle and the sterilizing effect is improved. The temperature of this sterilizer is 63° C. which is below the lower limit of the temperature which causes thermal shrinkage and sterilizing time is 10 seconds. Although this method has no problem of causing thermal shrinkage, there arises the problem that, since the sterilizing temperature is so low that the sterilizing time is prolonged and production efficiency thereby is decreased.

As another method for sterilizing a non-heat resistant plastic bottle without causing thermal shrinkage, there is known a method according to which the bottle is formed with a heat resistant plastic resin which does not cause thermal shrinkage at a normal sterilizing temperature within a range from 70° C. to 95° C. This method however has the problem that the heat resistant plastic resin is expensive and, besides, it requires many processes for forming the bottle with the result that the cost for manufacturing the bottle increases significantly.

Japanese Patent Application Laid-open Publication No. Hei 7-187149 discloses a method in which hot water is supplied to at least an inner surface of a plastic bottle and simultaneously cooling water which is of a lower temperature than the hot water is supplied to an outer surface of the bottle. According to this method, sterilizing can be completed without causing thermal shrinkage even in a case where high temperature water of e.g., 85° C. or over is injected into the inside of a non-heat resistant bottle. Likewise, there is disclosed a method according to which steam is injected in the inside of a bottle and simultaneously cooling water which is of a lower temperature than the steam is supplied onto the outer surface of the bottle to avoid occurrence of thermal shrinkage. Since, however, these bottle sterilizing methods cool the outer surface of the bottle with cooling water simultaneously with heating of the inner surface of the bottle with hot water or steam, difficulty arises in transmitting heat which is necessary for sufficiently sterilizing the inner surface of the bottle with the result that sterilizing time is prolonged and production efficiency is decreased and, further, as the sterilizing time is prolonged, a larger production line becomes necessary and the cost and space of equipment increase. Further, according to these methods, since the outer surface of the bottle is cooled with cooling water simultaneously with sterilizing of the inner surface of the bottle, in a case where it is necessary to sterilize the outer surface of the bottle also, the outer surface must be sterilized again with hot water with the result that two processes are required which necessitates further enlargement of the equipment.

The present invention has been made to solve the above described problems of the prior art method for sterilizing a plastic bottle in the aseptic filling system. It is an object of the invention to provide a method for sterilizing a plastic bottle capable of sterilizing a plastic bottle by a simple process and using heated sterilizing fluid such as hot water or a heated sterilizer at a normal sterilizing temperature within a range from 70° C. to 95° C. without causing deformation of the bottle due to thermal shrinkage.

DISCLOSURE OF THE INVENTION

Studies and experiments made by the inventors of the present invention for achieving the above described object of the invention have resulted in the finding, which has led to the present invention, that when heated sterilizing fluid such as hot water or a heated sterilizer at a temperature within a range from 65° C. to 90° C. is injected at least onto an inner surface of a bottle which is in an inflated state by producing a slightly positive pressure of 1 kPa-20 kPa in the bottle by causing the hot water or the heated sterilizer to be stored in a mouth portion of the bottle which is in an inverted state or by injecting air into the inside of the bottle, sterilizing of the inside of the bottle can be achieved in a short period of time without causing thermal shrinkage, even if the simultaneous cooling of the outer surface of the bottle is performed.

For achieving the above described object of the invention, there is provided a method for sterilizing a plastic bottle by injecting heated water or a heated sterilizer from a nozzle mouth of a bottle onto at least an inner surface of the bottle comprising a step of sterilizing the bottle while pressurizing and heating the inside of the bottle.

In one aspect of the invention, pressurizing of the inside of the bottle is achieved by inserting an injection nozzle into the nozzle mouth of the bottle in an inverted state and controlling an amount of flow which is discharged from the nozzle mouth of the bottle by adjusting the area of opening of the nozzle mouth.

In another aspect of the invention, there is provided a method for sterilizing a plastic bottle in which, in the above described process, cold water is injected on at least the inner surface or the outer surface of the bottle immediately after completion of sterilizing of the bottle thereby to quickly lower the temperature of the bottle to below a temperature at which thermal shrinkage occurs.

In another aspect of the invention, there is provided a method for sterilizing a plastic bottle wherein pressurizing of the inside of the bottle is achieved by maintaining internal pressure by inserting the injection nozzle into the nozzle mouth of the bottle in an inverted state and controlling the amount of flow which is discharged from the nozzle mouth of the bottle and thereby storing the heated water or the heated sterilizer in the inside of a nozzle portion or a shoulder portion of the inverted bottle, or by injecting air into the bottle or injecting both heated water or heated sterilizer and air.

According to the invention, by injecting heated sterilizing fluid such as heated water or heated sterilizer at a temperature of 65° C.-90° C. at least onto the inner surface of the bottle in which internal pressure is maintained by conducting sterilizing by pressurizing and heating the inside of the bottle, the inside of the bottle can be sterilized without causing thermal shrinkage of the bottle even if the simultaneous cooling of the outside of the bottle is not made. Therefore, compared with the prior art sterilizing method in which sterilizing is made at a temperature below 70° C. or the sterilizing method in which simultaneous cooling of the outside of the bottle is performed, sterilizing can be achieved in a shorter time and the cost and space for equipment can be saved with resulting improvement in the production efficiency. Further, according to the invention, since there is no need for using an expensive heat resistant plastic resin, the manufacturing cost can be saved as compared with the method using the heat resistant plastic resin.

In another aspect of the invention, pressurizing of the bottle (i.e., maintenance of a slightly positive pressure) can be achieved by controlling an amount of flow discharged from the nozzle mouth of the bottle.

In another aspect of the invention, in the above described method, cold water is supplied on at least the inner surface or the outer surface of the bottle immediately after completion of sterilizing of the bottle thereby to cool the bottle and quickly lower the temperature of the bottle to below a temperature at which thermal shrinkage occurs and, therefore, thermal history during a period of time from completion of sterilizing till time at which temperature of the bottle drops to a temperature below 70° C. at which thermal shrinkage occurs can be reduced as compared with a case where the bottle is left to cool naturally. As a result, deformation of the bottle can be prevented more perfectly.

Since, in still another aspect of the invention, pressurizing of the inside of the bottle is achieved by maintaining internal pressure by inserting the injection nozzle into the nozzle mouth of the bottle in an inverted state and controlling the amount of flow which is discharged from the nozzle mouth of the bottle and thereby storing the heated water or the heated sterilizer in the inside of a nozzle portion or a shoulder portion of the inverted bottle, or by injecting air into the bottle, maintenance of the internal pressure of the bottle during sterilizing at 1 kPa-20 kPa can be easily realized.

DESCRIPTION OF PREFERRED EMBODIMENTS

Embodiments of the invention will now be described with reference to the accompanying drawings.

Bottles to which the present invention is applied are non-heat resistant plastic bottles such as non-heat resistant PET bottles.

It is a feature of the method for sterilizing a bottle according to the invention to inject, in an aseptic filling system, heated sterilizing fluid at a temperature of 65° C.-90° C. at least onto an inner surface of a non-heat resistant plastic bottle in which the internal pressure is maintained at a slightly positive pressure.

As the internal pressure of the bottle, a slightly positive pressure within a range from 1 kPa to 20 kPa is necessary and a preferable range of the slightly positive pressure is 1-15 kPa and a more preferable range is 1-5 kPa.

As the heated sterilizing fluid, hot water or sterilizers such as peracetic acid, hydrogen peroxide and alkali respectively heated to 65° C.-90° C. can be used as the sterilizing fluid in the form of liquid. Preferable injection time of the heated sterilizing fluid is 3 seconds to 5 seconds. After sterilizing by the heated sterilizer, rinsing by e.g., warmed water may be made.

For maintaining the internal pressure of the bottle at a slightly positive pressure, supply of pressurized air to the inside of the bottle may be made in addition to supply of the heated water or heated sterilizer. In this method, an injection nozzle shown in the sectional view of FIG. 5, for example, may preferably be used. This injection nozzle is of a structure according to which heated water or heated sterilizer is supplied onto the inner surface of the bottle and an amount of flow of the heated water or heated sterilizer which is discharged is controlled to store the heated water or heated sterilizer in a mouth portion and a shoulder portion of the bottle while pressurized air is supplied to the inside of the bottle. The heated water or the heated sterilizer is injected from a first injection hole 2 and the pressurized air is injected from a second injection hole 3. The second injection hole 3 is communicated with an air reservoir 13a formed in a control plate 13 and this air reservoir 13a is connected to an outside pressurized air supply source.

Figure 1:
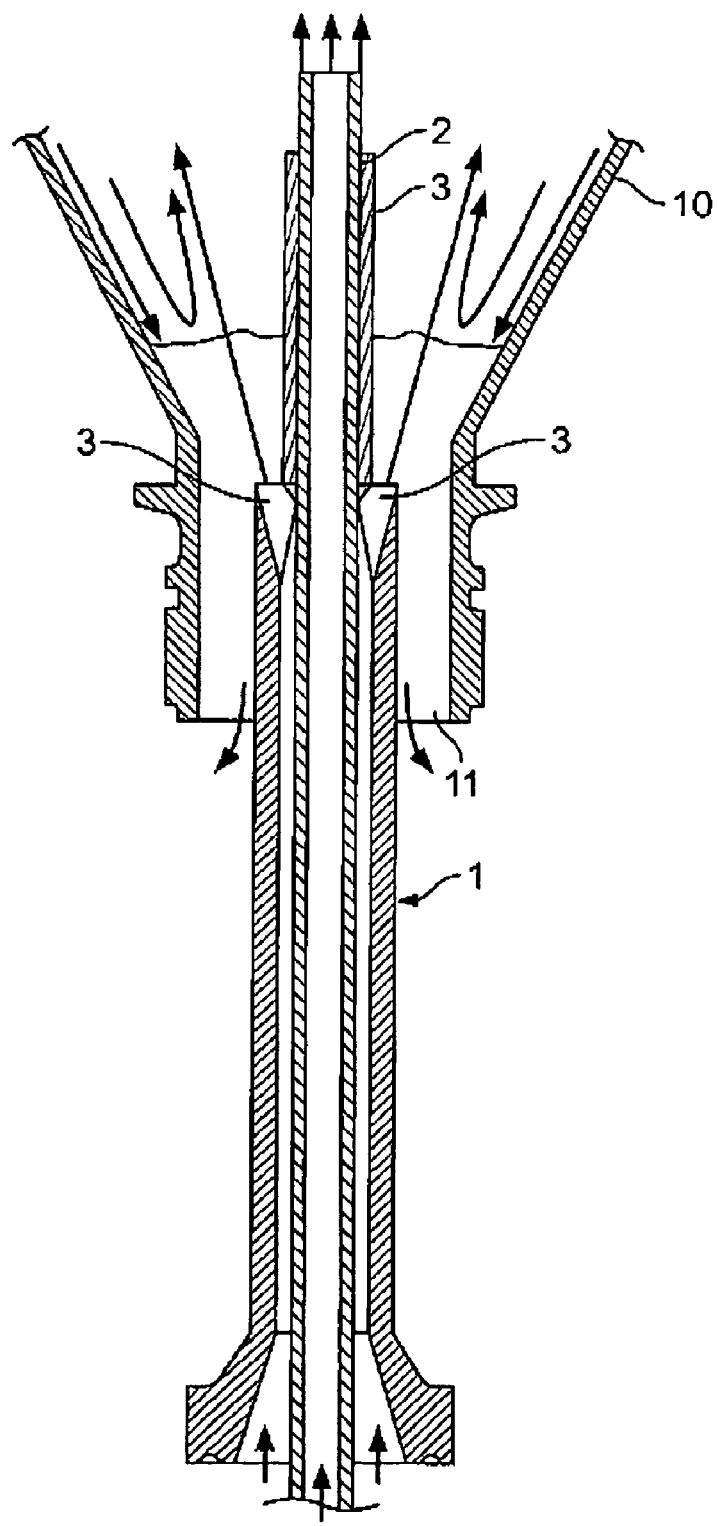
FIG. 1 is a partial sectional view of a bottle for illustrating a method for maintaining internal pressure of the bottle during sterilizing at a slightly positive pressure.

For causing the heated water or the heated sterilizer to be stored in the mouth portion of the inverted bottle, the outer diameter of the nozzle injecting the heated sterilizing fluid is made large to narrow the area between the nozzle and the nozzle mouth of the bottle. For example, the construction as shown in Japanese Patent Application Laid-open Publication No. 2003-181404 filed by the same applicant as the present application may be used. In this structure, the nozzle is a plural-stage nozzle having a first injection hole and a second injection hole with the second injection hole opening in stored heated water or sterilizer and the heated water or sterilizer is raised by injection from the second injection hole. More specifically, as shown in FIG. 1, heated sterilizing fluid injected from a first injection hole 2 formed in the foremost end portion of a sterilizing injection nozzle 1 which has been inserted in a mouth portion (nozzle mouth) 11 of an inverted bottle 10 and also injected from a second injection hole 3 opening in the lower portion thereof flows down to the mouth portion 11 after being injected. A part of the sterilizing fluid flowing down to the mouth portion 11 does not come out of the mouth portion 11 but stays in the mouth portion 11, for the gap between the nozzle 1 and the inner diameter of the mouth portion 11 is relatively small. The stored sterilizing fluid is stirred and raised by the sterilizing fluid injected from the second injection hole 3 and is scattered over the inner surface of the bottle 10 whereby sterilizing of the inside of the bottle 10 can be realized efficiently. By storing of the sterilizing fluid in the mouth portion 11, a slightly positive pressure within a range from 1 kPa to 20 kPa is produced in the bottle. In case there is no need for the scattering effect by raising of the sterilizing fluid, it will be sufficient to provide the first injection hole 2 only without providing the second injection hole 3.

In the embodiment of FIG. 1, the outer diameter of the nozzle is made large for causing a predetermined amount of the heated water or the heated sterilizer to be stored in the mouth portion of the bottle. Means for causing the heated water or the heated sterilizer to be stored in the mouth portion of the bottle is not limited to this but, alternatively, the heated water or the like may be stored in the mouth portion of the bottle by providing a blocking piece about the nozzle located in the mouth portion of the bottle, or providing a control plate in the nozzle portion under the mouth portion of the bottle and setting the distance between the control plate and the tip end of the mouth portion of the bottle suitably, or, in addition to such means, adjusting the area of the opening by suitably setting the outer diameter of the nozzle.

Figure 2:
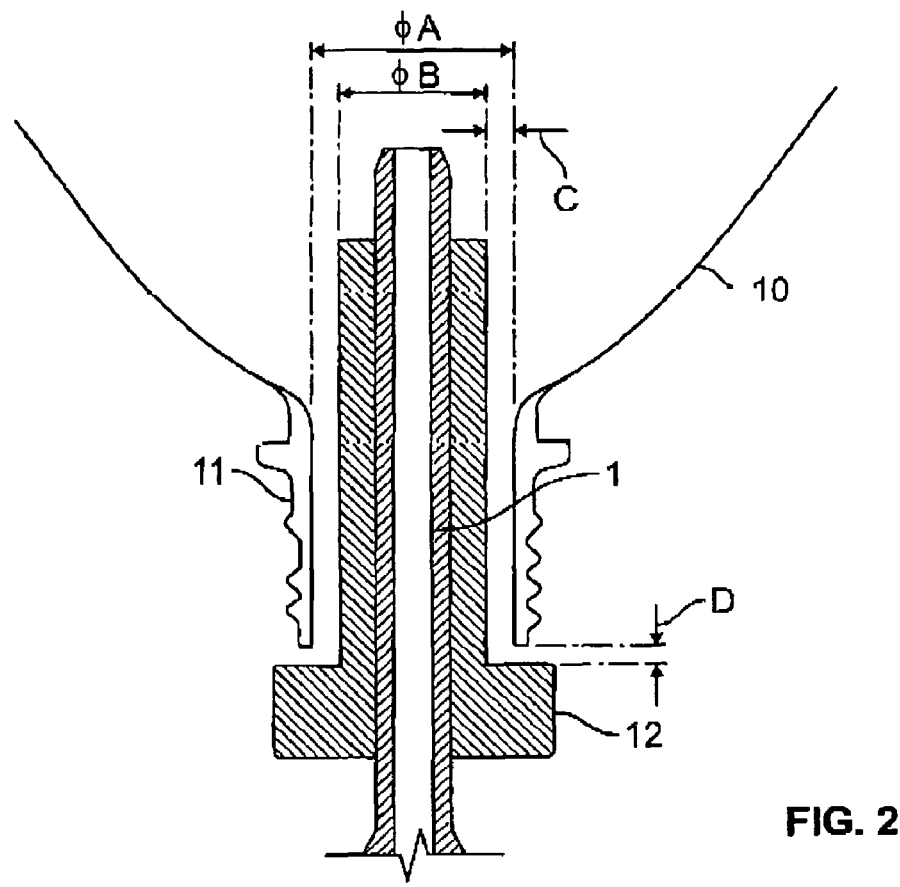
FIG. 2 is a partial sectional view of a bottle showing the shape of a nozzle for carrying out the method of the present invention.
Figure 3:
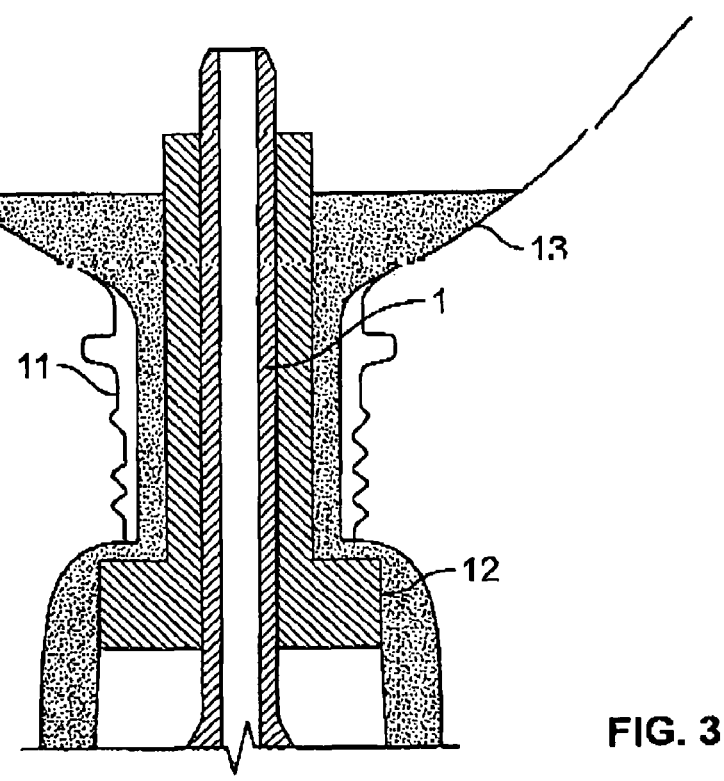
FIG. 3 is a partial sectional view showing operation of the nozzle.

FIG. 2 is a sectional view showing an example of a structure in which a control plate is provided in a portion of a nozzle under a mouth portion of a bottle. An injection nozzle 1 is formed with a control plate 12 in the form of a disk with a predetermined interval D between the lower end surface of a mouth portion 11. An amount of flow of discharged sterilizing fluid is controlled by a gap C between an inner diameter $\phi A$ of the mouth portion 11 of the bottle and an outer diameter $\phi B$ of the injection nozzle 1 and the gap D between the lower end surface of the bottle and the upper end surface of the control plate 12 and thereby is stored in the mouth portion 11 and a shoulder portion 13 of the bottle as shown in the sectional view of FIG. 3.

Figure 4:
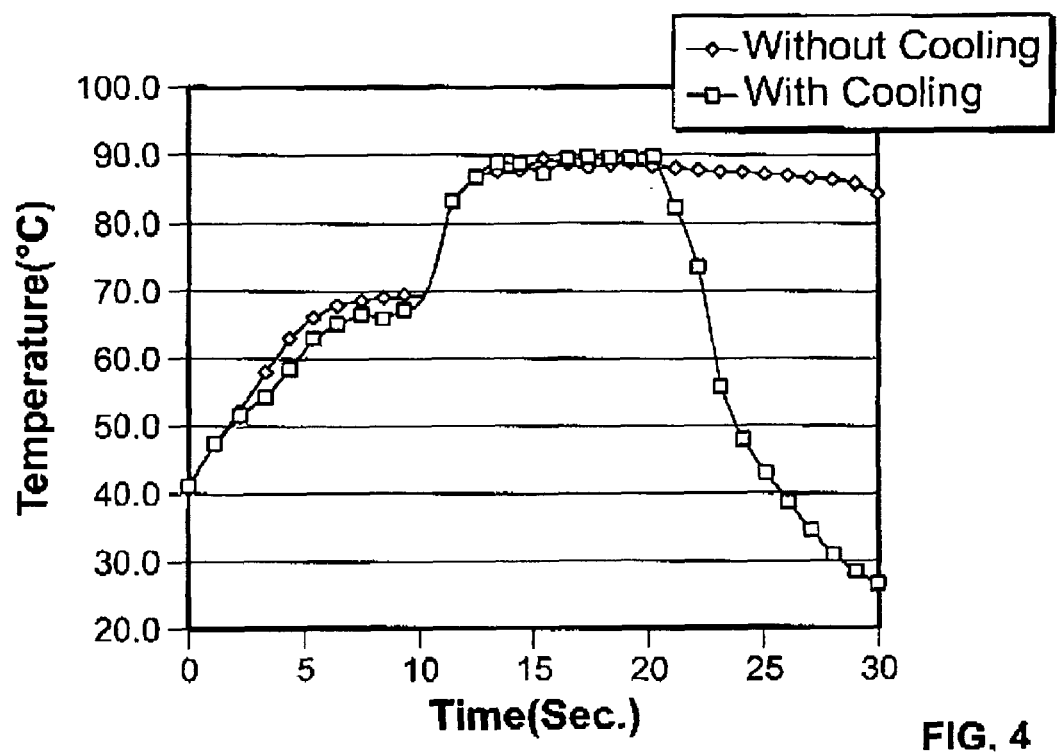
FIG. 4 is a graph showing natural cooling and cooling by cooling water of a bottle during sterilizing.

In a preferred embodiment of the invention, in the above described sterilizing method, by injecting cooling water at 5° C.-40° C. on the inner surface or the outer surface or on both the inner and outer surfaces of the bottle within 2 seconds from completion of sterilizing and thereby lowering the temperature of the bottle quickly to a temperature below a temperature at which thermal shrinkage occurs in the bottle, thermal history during a period of time from completion of sterilizing till time at which temperature of the bottle drops to a temperature below 70° C. at which thermal shrinkage occurs can be reduced as compared with a case where the bottle is left to cool naturally and, as a result, deformation of the bottle can be prevented more perfectly. For example, as shown in FIG. 4, in a case where an inner surface of a bottle is sterilized with temperature of sterilizing fluid being set at 87° C. and the bottle is left to cool naturally after sterilizing for a predetermined period of time, it takes a long time before the temperature of the bottle falls to below 70° C. and thermal shrinkage occurs in the bottle to some extent due to thermal history which the bottle uncergoes during this period of time. In a case where cooling water is injected on the bottle to cool the bottle, the temperature of the bottle drops sharply to a temperature below 70° C. and thermal history which the bottle undergoes during this period of time is much smaller than the case of natural cooling and, as a result, thermal shrinkage of the bottle can be held at minimum.

Immediately after completion of sterilizing, cooling water may be supplied from the nozzle mouth of the inverted bottle to the inside of the bottle and an amount of flow which is discharged from the nozzle mouth of the bottle may be controlled whereby internal pressure is produced in the inside of the bottle by storing the cooling water in the mouth portion and the shoulder portion of the inverted bottle and the bottle can be cooled while the pressure is maintained.

As cooling water used for cooling the bottle, ordinary water may be used but it is preferable to use drinkable water. Particularly, when cooling water is supplied to the inside of the bottle, water which has been sterilized under the same or better sterilizing conditions as contents to be filled in the bottle should preferably be used.

Figure 5:
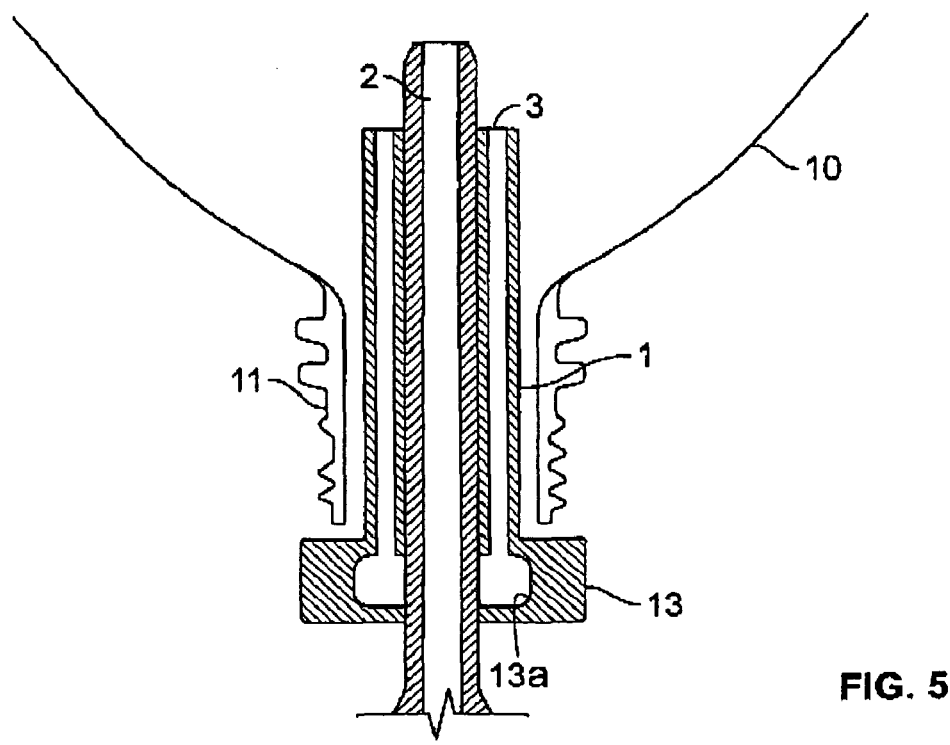
FIG. 5 is a partial sectional view for illustrating another example of a nozzle for carrying out the method of the present invention.

Prevention of thermal shrinkage of the bottle by supplying cooling water to the inner surface or the outer surfaces or to both the inner and outer surfaces of the bottle can be made simultaneously with supply of pressurized air to the inside of the bottle. FIG. 5 is a sectional view showing a structure in which cooling water is supplied to the inner surface of the bottle and an amount of flow of the cooling water which is discharged is controlled to store the cooling water in the inside of the mouth portion and the shoulder portion of the bottle while pressurized air is supplied to the inside of the bottle. Cooling water is injected from a first injection hole 2 and pressurized air is injected from a second injection hole 3. The second injection hole 3 is communicated with an air reservoir 13a formed in a control plate 13 and this air reservoir 13a is connected to an outside pressurized air supply source.

As the pressurized air used for cooling the bottle, air which has been sterilized under the same or better sterilizing conditions as contents to be filled in the bottle should preferably be used.

Example 1

An amount of change in full capacity of a bottle (i.e., an amount of change due to thermal shrinkage of the bottle) in a case where the bottle was kept in a positive pressure and the inner surface of the bottle was sterilized by heated water was observed.

(1) The Bottle Used

A bottle having a substantially circular cross section and having a waist portion (a narrow portion).
  Amount of full capacity=2000 ml
  Non-heat resistant PET bottle: weight 35 g.

(2) Injection Nozzle

A plural-stage nozzle shown in FIG. 5

Heated water was injected from the first injection hole and air sterilized by a filter was injected from the second injection hole.

The first injection hole was connected to a heated water tank via a valve and the second injection hole was connected to a pressurized air tank via a valve.

(3) Control Plate

A control plate having an air reservoir (communicated with the second injection hole) was used and the amounts of flow of liquid and air discharged during sterilizing of the bottle were controlled.

(4) Manner of Sterilizing

The bottle was inverted and the plural-stage nozzle was inserted from the nozzle mouth.

Heated water was injected from the first injection hole with a flow rate of 6 L/minute.

The heated water (temperature during injection) was adjusted to 55° C., 65° C., 75° C., 85° C. and 90° C.

The heated water adjusted to the respective temperatures was injected onto the inner surface of the bottle during 3 seconds, 10 seconds and 20 seconds.

(5) Method of Measuring the Internal Pressure

A needle having a lateral hole was attached to the tip portion of Environment-proof digital pressure sensor (expressed resolution of 0.01 kPa) made by Kabushiki Kaisha Keyence and this needle was mounted on the bottle to measure the internal pressure of the bottle during actual sterilizing.

(6) Adjustment of the Internal Pressure

The amount of flow (amount of injection) of air was adjusted by opening and closing the valve while observing the measured data of the bottle internal pressure to set average values of the bottle internal pressure during sterilizing at 0 kPa, 1 kPa, 2 kPa, 10 kPa, 20 kPa and 50 kPa. The injection of air was started after lapse of a predetermined period of time (1 to 2 seconds) from injection of the heated water, that is, after the heated water discharged was stored in the inside of the inverted bottle (excluding the case where the average value of the bottle internal pressure was 0 kPa). Cooling immediately after the sterilizing operation was not made. Results are shown in Table 1.

TABLE 1

| Bottle Internal pressure (kPa) | Sterilizing time (sec.) | Temperature(° C.) | | | | |
|---|---|---|---|---|---|---|
| | | 55 | 65 | 75 | 85 | 90 |
| 0 | 3 | ○ | X | X | X | X |
| | 10 | ○ | X | X | X | X |
| | 20 | ○ | X | X | X | X |
| 1 | 3 | ○ | ○ | ○ | X | X |
| | 10 | ○ | ○ | ○ | X | X |
| | 20 | ○ | ○ | ○ | X | X |
| 2 | 3 | ○ | ○ | ○ | X | X |
| | 10 | ○ | ○ | ○ | X | X |
| | 20 | ○ | ○ | ○ | X | X |
| 10 | 3 | ○ | ○ | ○ | ○ | ○ |
| | 10 | ○ | ○ | ○ | ○ | ○ |
| | 20 | ○ | ○ | ○ | X | X |
| 20 | 3 | ○ | ○ | ○ | ○ | ○ |
| | 10 | ○ | ○ | ○ | ○ | ○ |
| | 20 | ○ | ○ | ○ | X | X |
| 50 | 3 | X X | X X | X X | X X | X X |
| | 10 | X X | X X | X X | X X | X X |
| | 20 | X X | X X | X X | X X | X X |

No change ○ (when the change in the bottle capacity was ±1% the bottle capacity before sterilizing was judged to be good.) (2000 ml ± 20 ml)
Deformed by shrinkage X (shrinkage occurred by more than 1% from the bottle capacity before sterilizing)
Deformed by inflation X X (inflation occurred by more than 1% from the bottle capacity before sterilizing)

From Table 1, (1) In case the bottle internal pressure was 0 kPa, there was no significant change in the amount of the full capacity of the bottle when the temperature of the heated water was 55° C. regardless of sterilizing time (duration of time during which heated water was injected) and thermal shrinkage caused by heating was substantially prevented.

When, however, the temperature of the heated water exceeded 65° C., the amount of the full capacity of the bottle was reduced and thermal shrinkage caused by heating is considered to have occurred.

From this, when the bottle internal pressure is 0 kPa, it is considered that sterilizing by heated water for a certain period of time causes thermal shrinkage to start as the temperature of the heated water exceeds about 60° C. which is a middle region in the range of 55° C.-65° C. of the example.

In case the temperature of the heated water is below 55° C. (60° C.), it is difficult to achieve a sufficient sterilizing effect depending upon the sterilizing time and such temperature range is not a practical temperature range.

(2) When the bottle internal pressure was 1 kPa and 2 kPa, there was no significant change in the amount of the full capacity of the bottle in case the temperature of the heated water was up to 75° C. regardless of sterilizing time (duration of time during which heated water was injected) and thermal shrinkage caused by heating was substantially prevented by the internal pressure.

When the temperature of the heated water largely exceeded a temperature range (60-70° C.) which is normally used in sterilizing an amorphous bottle, the amount of the full capacity of the bottle was reduced.

In case the bottle internal pressure was 1 kPa and 2 kPa, it was confirmed that, when the temperature of the heated water is within a practical range, the amount of injection of pressurized air was held at a low value with the result that sterilizing was made efficiently regardless of the sterilizing time (duration of time during which the heated water was injected). Thus, it was found that thermal shrinkage due to heating for sterilizing was prevented by maintaining the bottle internal pressure during sterilizing at a positive pressure.

(3) In case the bottle internal pressure was 10 kPa and 20 kPa, when sterilizing was made by the heated water at 85° C. or 90° C. for 20 seconds, the bottle was deformed by protruding outwardly due to the internal pressure without causing thermal shrinkage. In practical sterilizing time and temperature range of the heated water, however, no significant change took place in the amount of the full capacity of the bottle and thermal shrinkage could be prevented by the internal pressure and it was found that thermal shrinkage due to heating for sterilizing could be prevented by maintaining the bottle internal pressure during sterilizing at a positive pressure.

(4) In case the bottle internal pressure was 50 kPa, the bottle used in this example which was of a relatively light weight and a small thickness was deformed by protruding outwardly by the internal pressure.

(5) In the above described Example 1, observation was made about the amount of the full capacity of the bottle (amount of change due to thermal shrinkage of the bottle) in case the internal pressure was maintained at a predetermined value by first injecting heated water in the inside of the inverted bottle and then starting injection of air after the heated water was stored in the inside of the bottle.

Observation was also made about the amount of change in the full capacity of the bottle (amount of change due to thermal shrinkage of the bottle) in case the internal pressure was maintained at a predetermined value by injecting heated water and pressurized air simultaneously in the inside of the inverted bottle and supplying a larger amount of pressurized air than in the case of Example 1 without storing the heated water (without changing other conditions). In this case, about the same result as in the case of Example 1 was obtained.

From this result, it was found that, regardless of means for maintaining the internal pressure, conducting sterilizing while maintaining the inside of the bottle at a positive pressure could realize sterilizing efficiently without causing thermal shrinkage due to heating even when a bottle of a light weight and a small thickness is used.

(6) In the above described Example 1, heated water was used as heating medium.

The amount of change in the full capacity of the bottle (amount of change due to thermal shrinkage of the bottle) was observed by heating a peraceptic acid type sterilizer (product name: TOYO-ACTIVE) with concentration of peraceptic acid being 2000 ppm-3000 ppm as the heating medium and conducting a test for sterilizing the bottle in the same manner as in Example 1 without changing other conditions.

In this case, about the same result as in the case of Example 1 was obtained and difference due to the heating medium could not be observed.

Example 2

As a bottle, a 2000 ml non-heat resistant PET bottle (weight being 53 g) of a cylindrical shape (i.e., a shape having no pressure reducing panel) was used. As sterilizing means, the heated water injection nozzle shown in FIG. 2 which is of a type in which heated water was stored in the nozzle mouth portion and the shoulder portion was used in the manner shown in FIG. 3. Heated water was injected onto the inner surface of the bottle at a flow rate of 6 L/minute at sterilizing temperature of 90° C. for 3 seconds while maintaining internal pressure of the bottle at 2 kPa during sterilizing. Immediately after completion of sterilizing, cooling aseptic water at 30° C. was injected onto the inner surface of the bottle at a flow rate of 12 L/minute for 0 second, 1 second and 2 seconds to cool the bottle while supplying pressurized air to the inside of the bottle to keep the internal pressure at 2 kPa. Then the amount of change in the full capacity of the bottle was measured. As a comparative example, sterilizing of the bottle was conducted and the amount of change in the full capacity of the bottle was measured under the same conditions as in Example 2 excepting that no internal pressure was produced in the bottle by causing the heated water to flow straightly without causing storing of the heated water. Results of these measurements are shown in Table 2.

TABLE 2

| Method | cooling time (sec.) | amount of shrinkage (ml) |
| --- | --- | --- |
| Storing heated water (internal pressure is maintained) | 0 | −12 |
| | 1 | 2 |
| | 2 | 7 |
| Flowing straight (no internal pressure) | 0 | −24 |

As will be apparent from Table 2, it was found that, by combining sterilizing at 90° C. with the internal pressure of the bottle being maintained at 2 kPa and cooling the bottle immediately after completion of sterilizing while maintaining the internal pressure, shrinkage of the bottle could be prevented. In contrast, in the comparative example, shrinkage occurred in the bottle before conducting cooling.

The invention claimed is:

1. A method for sterilizing a plastic bottle by injecting heated water or a heated sterilizer from a nozzle mouth of a bottle onto at least an inner surface of the bottle comprising a step of sterilizing the bottle while pressurizing and heating the inside of the bottle and a step of cooling the bottle by supplying cold water on at least the inner surface or the outer surface of the bottle beginning immediately after completion of sterilizing of the bottle.

2. A method as defined in claim 1 wherein sterilizing of the inside of the bottle by the heated water or the heated sterilizer is made by injecting the water or sterilizer which is heated to 65° C.-90° C. for 3 to 20 seconds.

3. A method as defined in claim 1 wherein the bottle is cooled by supplying cold water while supplying pressurized air into the inside of the bottle.

4. A method as defined in claim 1 wherein cooling of the bottle is made by supplying cold water of 5° C.-40° C. on the outer surface of the bottle within 2 seconds after completion of sterilizing of the bottle.

5. A method as defined in claim 1 wherein the step of sterilizing the bottle is made by simultaneously sterilizing the outer surface of the bottle.

* * * * *